United States Patent
Fujita (10) Patent No.: US 7,372,575 B2
(45) Date of Patent: May 13, 2008

(54) OPTICAL TOMOGRAPHIC APPARATUS

(75) Inventor: Hiroshi Fujita, Saitama (JP)

(73) Assignee: Fujinon Corporation, Saitama (JP)

( * ) Notice: Subject to any disclaimer, the term of this patent is extended or adjusted under 35 U.S.C. 154(b) by 308 days.

(21) Appl. No.: 11/293,270

(22) Filed: Dec. 5, 2005

(65) Prior Publication Data
US 2006/0146339 A1 Jul. 6, 2006

(30) Foreign Application Priority Data
Dec. 6, 2004 (JP) .......................... P.2004-352458

(51) Int. Cl.
*G01B 9/02* (2006.01)
*G01B 11/02* (2006.01)
(52) U.S. Cl. ...................... 356/479; 356/497
(58) Field of Classification Search ................. 356/479, 356/484, 497
See application file for complete search history.

(56) References Cited

U.S. PATENT DOCUMENTS

| | | | | |
|---|---|---|---|---|
| 5,301,010 | A * | 4/1994 | Jones et al. .................. | 356/479 |
| 6,198,540 | B1 * | 3/2001 | Ueda et al. .................. | 356/479 |
| 6,538,817 | B1 * | 3/2003 | Farmer et al. .............. | 359/618 |
| 6,611,339 | B1 * | 8/2003 | Yang et al. .................. | 356/485 |
| 6,842,254 | B2 * | 1/2005 | Van Neste et al. .......... | 356/497 |
| 6,934,035 | B2 * | 8/2005 | Yang et al. .................. | 356/485 |
| 7,126,693 | B2 * | 10/2006 | Everett et al. .............. | 356/479 |
| 7,251,038 | B2 * | 7/2007 | Mcinnes et al. ............. | 356/479 |

(Continued)

FOREIGN PATENT DOCUMENTS

JP 2003-254898 A 9/2003

(Continued)

OTHER PUBLICATIONS

Sato et al., Optics vol. 32, No. 4 (2003) pp. 268-274.

(Continued)

*Primary Examiner*—Patrick Connolly
(74) *Attorney, Agent, or Firm*—Birch, Stewart, Kolasch & Birch, LLP (57) ABSTRACT

An optical tomographic apparatus is provided and includes a light source portion, an interferometer, and a signal processing portion. The light source portion including two low coherent light sources capable of simultaneously emitting light having wavelength bands different from each other. The emitted light is divided in two of a light flux irradiated to a subject by a probe and a light flux irradiated to reference mirrors that is divided by a dichroic mirror into light fluxes for respective wavelength bands. The reference light from the reference mirrors is combined with detected light from the subject to provide interference light. An optical detector detects the interference light for respective wavelength bands by a spectroscopic optical system, and a signal processing portion processes the detected light to provide optical tomographic images with regard to different portions of the subject for respective wavelength bands.

5 Claims, 4 Drawing Sheets

U.S. PATENT DOCUMENTS

| | | | |
|---|---|---|---|
| 2003/0112444 A1* | 6/2003 | Yang et al. | 356/486 |
| 2004/0075841 A1* | 4/2004 | Van Neste et al. | 356/497 |
| 2004/0109164 A1 | 6/2004 | Horii et al. | |
| 2005/0057756 A1* | 3/2005 | Fang-Yen et al. | 356/497 |
| 2005/0105097 A1* | 5/2005 | Fang-Yen et al. | 356/497 |
| 2005/0219544 A1* | 10/2005 | Chan et al. | 356/497 |
| 2006/0146338 A1* | 7/2006 | Fujita | 356/479 |
| 2007/0239031 A1* | 10/2007 | Lee et al. | 600/473 |

FOREIGN PATENT DOCUMENTS

| | | |
|---|---|---|
| JP | 2003-307485 A | 10/2003 |
| JP | 2003-329577 A | 11/2003 |
| WO | WO-03/062802 A | 7/2003 |

OTHER PUBLICATIONS

Yingtian Pan, Daniel L. Farkas et al,. Journal of Biomedical Optics, vol. 3, No. 4, pp. 446-455 left-hand column, paragraph, Second-p. 448 right-hand column, paragraph Third.(Oct. 1998).

V.M. Gelekonov, G.V. Gelikonov, F. I. Feldchtein, "Two-Wavelength Optical Coherence tomography" Radiophysics and Quantum Electronics, vol. 47, No. 10-11, pp. 848-859, XP002367745 (Nov. 2004).

* cited by examiner

OPTICAL TOMOGRAPHIC APPARATUS

FIELD OF THE INVENTION

The present invention relates to an optical tomographic apparatus used in providing a tomographic image of a subject in a medical or industrial field or the like.

BACKGROUND OF THE INVENTION

In recent years, in a field of taking an image of a subject for medical use, industrial use or the like, particularly, in a field of an electronic endoscope, there is known an apparatus of taking a tomographic image of a subject by using a method of OCT (optical coherence tomography).

According to the tomographic apparatus by OCT, light is used as a detecting probe and therefore, there is not posed a problem that a subject is exposed to X-ray irradiation as in an X-ray imaging apparatus of a related art, and the apparatus is extremely preferable particularly when the subject is the human body. Further, a large-sized apparatus of CT, MRI or the like is not needed, the subject can simply be inspected and therefore, a burden of the subject in view of cost or a burden in view of a physical strength thereof can be alleviated and the apparatus is preferable also in this respect.

Further, according to the tomographic apparatus using OCT, by utilizing low coherence of light having a spectrum width in a wide band, interference wave information at respective positions in a depth direction of the subject is provided and therefore, reflected light from an inner portion of the subject can be detected by a spatial resolution of μm order, and a measurement resolution can considerably be promoted in comparison with that of the X-ray imaging apparatus of the background art.

The tomographic apparatus using OCT having a number of excellent characteristics in this way is disclosed in, for example, Optics vol. 32, No. 4 (2003): Manabu Sato, Naohiro Tanno. Further, there is specifically proposed a tomographic apparatus using OCT which is technically devised variously (refer to, for example, JP-A-2003-329577 or the like).

However, it is a current state that an apparatus which is satisfactory in a speed of acquiring image information with regard to a subject, an amount of information thereof or the like has not been necessarily proposed and reduced into practice and a further improvement has been desired.

Particularly, when an optical tomographic apparatus is used for medical use, it is necessary to make a physical or spiritual burden on a subject in accordance with inspection as small as possible and for that purpose, there is desired an apparatus capable of acquiring a tomographic image with regard to a number of affected portions by a number of times of irradiation as small as possible.

SUMMARY OF THE INVENTION

The invention has been carried out in view of such a situation and an object of an illustrative, non-limiting embodiment of the invention is to provide an optical tomographic apparatus capable of acquiring more tomographic image information with regard to a subject by an irradiation time period as small as possible. Also, the invention is not required to solve the above-described problems, and an illustrative, non-limiting embodiment of the invention may solve a different problem or may not solve any problems.

An illustrative, non-limiting of an optical tomographic apparatus of the invention is characterized in comprising:

a light source for emitting light having low coherence in at least two wavelength bands different from each other;

an interferometer providing interference light by diving a light flux emitted from the light source in two fluxes, irradiating a subject with one of the two fluxes, irradiating a reference face with the other of the two fluxes, and combining a light flux reflected from the subject and a light flux reflected from the reference face, and provide an optical intensity distribution of the interference light by an optical detector; and a signal processing portion for providing a tomographic image signal based on a signal of the optical intensity distribution provided by the interferometer;

wherein the interferometer comprises a wavelength selecting element for separating the light flux irradiated to the reference face into at least a light flux of a first wavelength band and a light flux of a second wavelength band without producing a phase shift therebetween, and reflection optical elements having the reference faces respectively for the light fluxes separated by the wavelength selecting element, and the signal processing portion generates the tomogrphic image signal for the respective wavelength bands of the light source and outputs a combined signal thereof Further, it is preferred that the optical detector comprises a line image sensor, the interferometer comprises a spectroscopic optical system for separating the interference light, and by irradiating the line image sensor with the interference light by way of the spectroscopic optical system, the line image sensor is able to detect to the interference light separated for the respective wavelength bands of the light source.

Further, it is preferred that a moving mechanism is provided to move the respective reflection optical elements in respective optical axis directions, wherein an optical path length of the reference light flux reflected from the reference face is able to be changed for the respective wavelength bands of light irradiated to the respective reflection optical elements.

According to the optical tomographic apparatus of the invention, optical tomographic images with regard to different portions in a depth direction of the subject from a vicinity of a surface thereof to a depth portion thereof can efficiently be acquired by a small irradiation time period.

Further, fluxes of low coherent light having different wavelength bands are simultaneously irradiated to the subject and therefore, an operation of switching the light sources for respective wavelength bands is dispensed with, the operability is excellent, further, optical tomographic image information more than that in the related art can be acquired by a small inspection time period.

Further, by adjusting positions of the reference mirrors provided for the respective wavelength bands, with regard to the same portion of the subject, fluxes of interference light at the respective wavelength bands can be provided and therefore, a spectroscopic characteristic with regard to the portion of the subject can easily be acquired.

DETAILED DESCRIPTION OF THE INVENTION

An explanation will be given of an optical tomographic apparatus according to an exemplary embodiment of the invention in reference to the drawings as follows.

Figure 1:
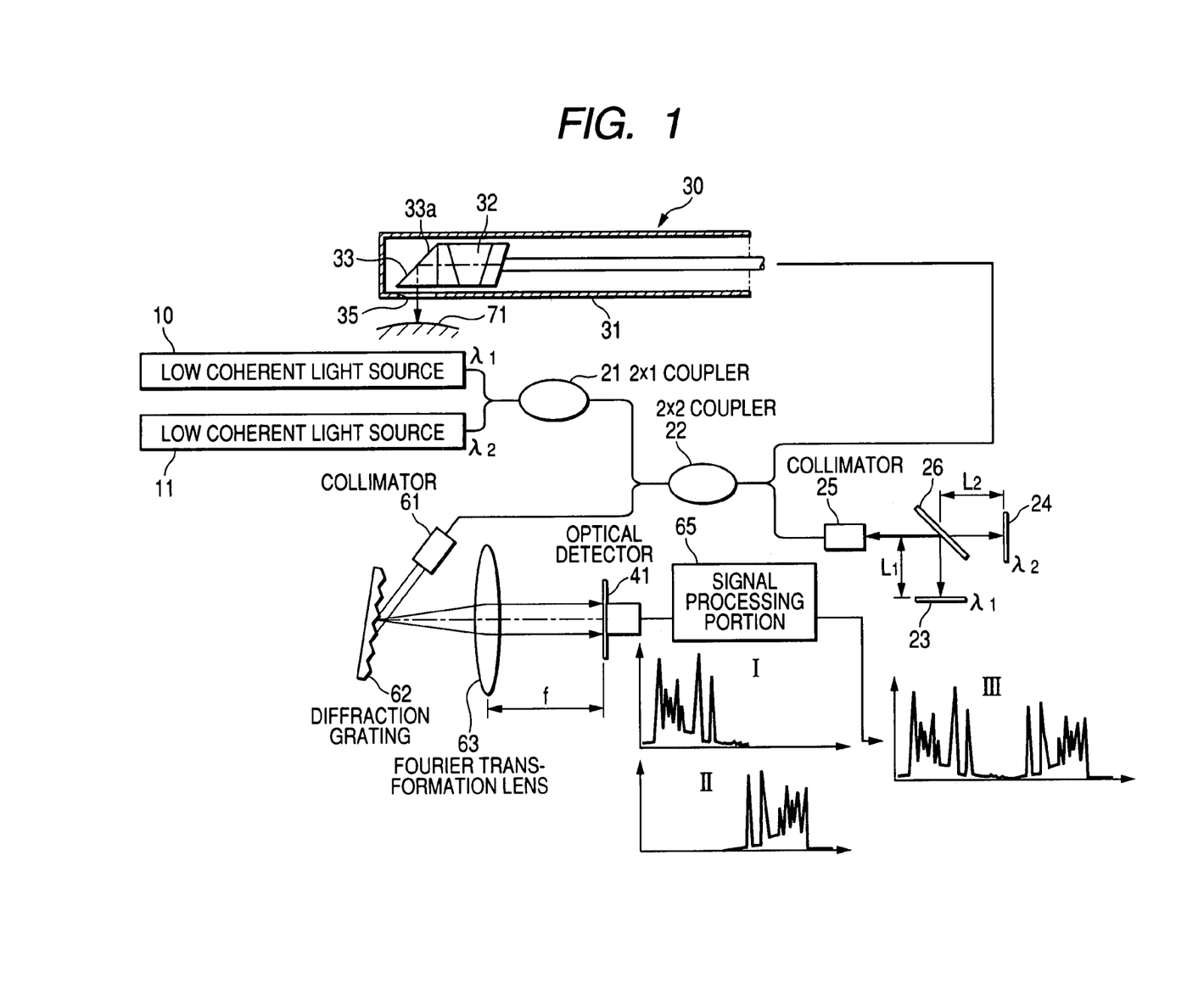
FIG. 1 is an outline view showing an optical tomographic apparatus according to an illustrative, non-limiting first embodiment of the invention.

FIG. 1 is an outline view showing an optical tomographic apparatus according to an exemplary first embodiment of the invention.

The optical tomographic apparatus according to the embodiment is applied to, for example, an endoscope for medical use and mainly include a light source portion, an interferometer and a signal processing portion.

Figure 4:
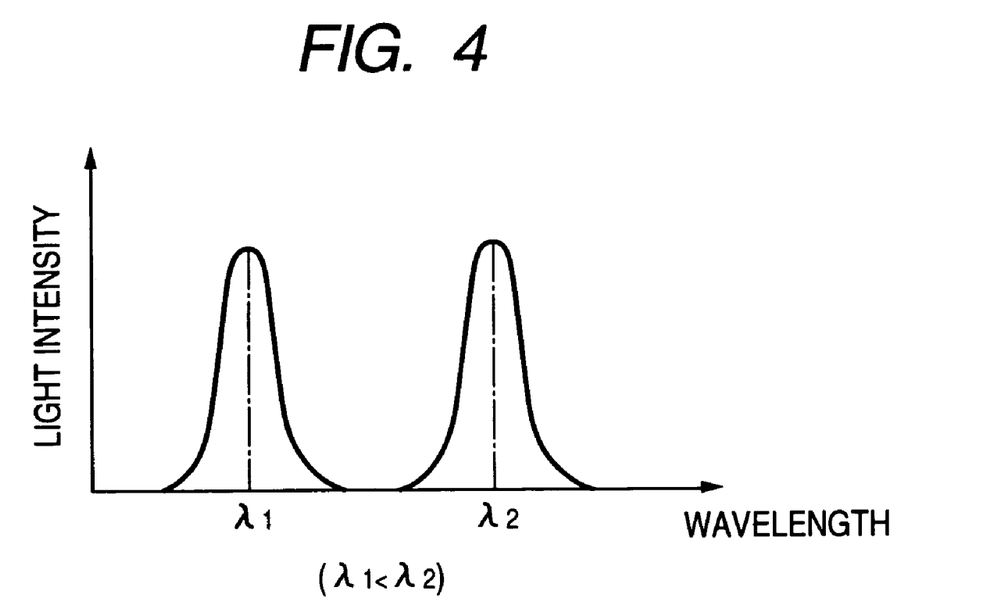
FIG. 4 is a diagram showing an example of a profile of output light of a low coherent light source.

The light source portion includes two of low coherent light sources 10, 11. The two low coherent light sources 10, 11 output fluxes of light respectively having different wavelength bands, for example, as shown by FIG. 4, whereas the first low coherent light source 10 outputs low coherent light having a peak value at a wavelength $\lambda_1$ and having a beam width, the second low coherent light source 11 outputs low coherent light having a peak value at a wavelength $\lambda_2$ ($\lambda_1 < \lambda_2$) and having a beam width. Further, it is preferable to select the first and the second low coherent light sources 10, 11 such that profiles of fluxes of output light do not overlap each other as shown by FIG. 4.

An interferometer constitutes a so-called Michelson type interferometer as a whole and includes 2×2 coupler 21 and a 2×2 coupler 22 for dividing and/or combining a light flux(es) guided by an optical fiber (indicated in the drawing by a black bold line) as a waveguide, a probe 30 for acquiring tomographic image information from a subject 71, two reference mirrors 23, 24 as reflecting optical elements, and an optical detector 41 for photoelectrically converting interference light incident by way of a spectroscopic optical system, mentioned later.

Further, a collimator 25 is connected to the optical fiber between the 2×2 coupler 22 and the two reference mirrors 23, 24, and a dichroic mirror 26 as a wavelength selecting element is arranged between the collimator 25 and the first and the second reference mirrors 23, 24. Here, the collimator 25, the dichroic mirror 26, and the second reference mirror 24 are arranged on the same optical axis such that light emitted from the collimator 25 passes a center of the dicroic mirror 26 and is irradiated to a center of the second reference mirror 24.

On the other hand, the first reference mirror 23 is arranged in a direction orthogonal to the optical axis between the collimator 25 and the second reference mirror 24 as described above. That is, the first reference mirror 23 is arranged at a position which is irradiated with light emitted from the collimator 25 and orthogonally reflected by the dichroic mirror 26.

Further, a distance between the dichroic mirror 26 and the first reference mirror 23 is set to a value $1_1$, further, a distance between the dichroic mirror 26 and the second reference mirror 24 is set to a value $1_2$, respectively, further, the distances satisfy a relationship of $1_1 \neq 1_2$. This is for separating a tomographic image signal by low coherent light centering on the wavelength $\lambda_1$ and a tomographic image signal by low coherent light centering on the wavelength $\lambda_2$ as mentioned later.

On the other hand, according to the probe 30, as shown by FIG. 1, inside of a flexible sheath 31 contains a GRIN lens 32 and a right angle prism 33 as an object optical system along with the optical fiber such that the right angle prism 33 is disposed on a front end side of the probe 30. Further, the right angle prism 33 reflects to deflect an optical path by 90 degrees at an inclined face 33a to achieve a function of emitting light from one of orthogonal faces of the right angle prism 33. Further, it is preferable to arrange a center of the inclined face 33a of the right angle prism 33 to pass an optical axis of the GRIN lens 32.

Further, the sheath 31 includes a light transmitting window 35 in a peripheral direction of a vicinity at which the right angle prism 33 is disposed to enable to irradiate low coherent light deflected by 90 degrees by the right angle prism 33 to the subject 71 at outside of the probe 30 and enable to acquire back scattered light returning from the subject 71.

Further, although in FIG. 1, a structure of the probe 30 is simply illustrated in order to facilitate understanding by simplifying the explanation, actually, at least a portion arranged with the GRIN lens 32 and the right angle prism 33 constitutes a member substantially in a shape of a hollow cylinder integrally formed with the sheath 31 by using a comparatively rigid member which is different from the flexible member forming the sheath 31 to achieve a function of protecting the GRIN lens 32 and the right angle prism 33.

Further, although according to the probe 30, the right angle prism 33 may be fixedly provided at inside of the probe 30 and the probe 30 per se may be pivoted, further preferably in view of operability or the like, as described later, there may be constituted a constitution in which the right angle prism 33 can freely be rotated by providing a pivoting mechanism constituting a pivoting axis by the optical axis of the GRIN lens.

Figure 2:
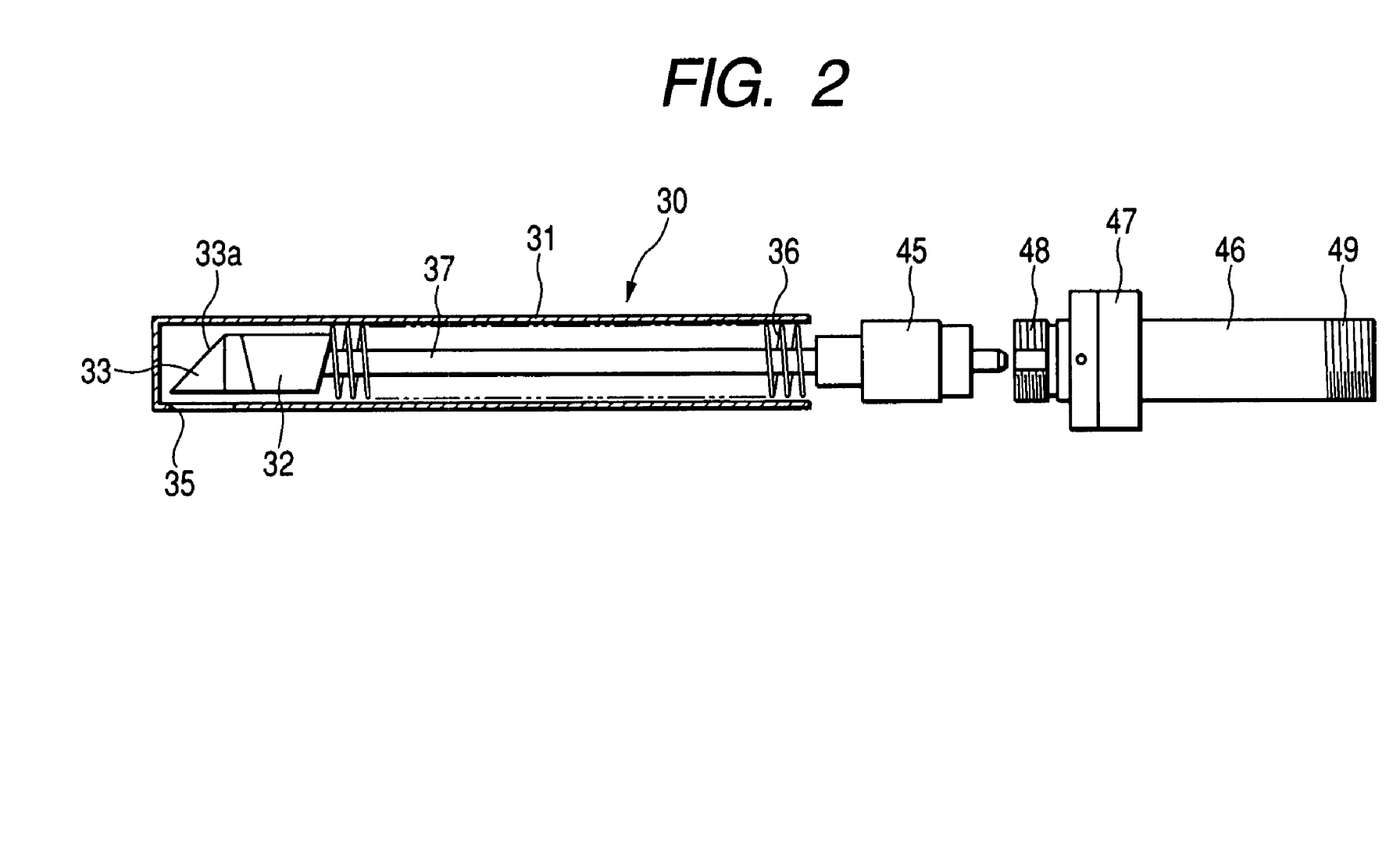
FIG. 2 is an outline sectional view showing a constitution when a probe is provided with a pivoting mechanism.

FIG. 2 shows a constitution example of a pivoting mechanism for pivoting the right angle prism 33 and the pivoting mechanism will be explained in reference to the drawing as follows.

According to the constitution example, the sheath 30 inside contains a spiral spring 36 in series up to a side of a base end of the sheath 30 to be brought into contact with a portion of the GRIN lens 32 on a side opposed to a portion at which the right angle prism 33 is disposed, so as to enable to pivot integrally the GRIN lens 32 and the right angle prism 33 along with a fiber handle 37 centering on the optical axis of the GRIN lens 32.

That is, the fiber handle 37 is connected to a plug 45 fixedly attached to the base end portion of the sheath 30, and the plug 45 is attached with a rotation operation portion 46 by being screwed to a receptacle 48 formed at the rotation operating portion 46.

The rotation operating portion 46 is formed with a receptacle 48 at one end portion thereof and a receptacle 49 at the other end portion thereof and provided with an operating ring 47 at an outer peripheral portion thereof Further, whereas the receptacle 48 on the front end side is connected to the plug 45 provided at the base end portion of the sheath 30 as mentioned above, the other receptacle 49 is connected to the 2×2 coupler 22 by way of the optical fiber. Further, by pivoting the operating ring 47, the spiral spring 36, the fiber handle 37, the GRIN lens 32 and the right angle prism 43 can integrally be pivoted centering on the optical axis of the GRIN lens 32. Further, in this case, it is preferable to form a plurality of the light transmitting window portions 35 or continuously form the light transmitting window portions 35 in the peripheral direction to enable light to come and go to and from an arbitrary portion in the peripheral direction of the probe 30.

The interferometer is further provided with the spectroscopic optical system including a constitution, mentioned later, and interference light provided by the 2×2 coupler 22 is guided to the optical detector 41 by way of the spectroscopic optical system.

That is, the spectroscopic optical system includes a collimator 61, a diffraction grating 62 and a Fourier transformation lens 63. Interference light is guided from the preceding 2×2 coupler 22 to the collimator 61 by way of the optical fiber, the interference light is made to be parallel light by the collimator 61 and irradiated to the diffraction grating 62 of a reflection type.

The diffraction grating 62 is provided at a front side focal position of the Fourier transformation lens 63, diffraction light from the diffraction grating 62 transmits through the Fourier transformation lens 63 and is irradiated to the optical detector 41 provided at a post stage of the Fourier transformation lens 63 at a position remote therefrom by a focal length f. Further, the optical detector 41 is preferably, for example, a so-called line image sensor or the like.

Here, by subjecting diffraction light from the diffraction grating 62 to Fourier transformation operation by the Fourier transformation lens 63, detected light and reference light are overlapped in a spectrum region to form interference spectrum in accordance with interference of optical waves on the optical detector 41. That is, in other words, a power spectrum combined with detected light and reference light is incident on the optical detector 41.

An output of the optical detector 41 is inputted to a signal processing portion 65. At the signal processing portion 65, an input signal from the optical detector 41 is subjected to a signal processing necessary for acquiring a one-dimensional tomographic image signal reflected with information in a depth direction of the subject 71, and a tomographic image signal with regard to a portion of the subject 71 irradiated with low coherent light is provided from the signal processing portion 65. Further, by subjecting the tomographic image signal provided in this way to a processing necessary for generating a tomographic image at a publicly known/well known image processing portion, not illustrated, the tomographic image can be displayed on a display apparatus, not illustrated.

Next, a total operation of the embodiment apparatus will be explained.

When fluxes of low coherent light are simultaneously emitted from the first and the second low coherent light sources 10, 11, fluxes of emitted light are combined at the 2×1 coupler 21, transmitted to the 2×2 coupler 22, here, divided into two of light transmitted to the probe 30 and light transmitted to the reference mirrors 23, 24.

Light transmitted to the probe 30 is guided to the GRIN lens 32 and is incident on the light angle prism 33 by way of the GRIN lens 32, deflected by 90 degrees by the inclined face 33a of the light angle prism 33, passes through the light transmitting window portion 35 and is irradiated to the subject 71 at outside of the probe 30. That is, the subject 71 is simultaneously irradiated with low coherent light having the central wavelength of $\lambda_1$ and low coherent light having the central wavelength of $\lambda_2$.

Fluxes of light having different wavelength bands irradiated to the subject 71 in this way advance to the inner portion of the subject 71, reach depth positions which respectively differ from each other in accordance with the wavelength bands, and respectively generate fluxes of back scattered light at respective tomographic boundary portions at which refractive index distributions mainly become discontinuous. The respective fluxes of back scattered light generated at the respective tomographic boundary portions in the depth direction are provided with slight coherence, advance inversely through the irradiation path as fluxes of the detected light, pass through the light transmitting window portion 35 of the probe 30 and return to the inclined face 33a of the right angle prism 33, deflected by 90 degrees and return to the 2×2 coupler 22 by way of the GRIN lens 32 and the optical fiber.

On the other hand, other light flux divided in two preceedingly at the 2×2 coupler 22 is made to be parallel light by the collimator 25 and is irradiated to the dichroic mirror 26. Further, at the dichroic mirror 26, by a spectroscopic characteristic thereof, whereas low coherent light having the central wavelength of $\lambda_1$ is deflected by 90 degrees relative to the irradiating direction to be irradiated to the first reference mirror 23, low coherent light having the central wavelength of $\lambda_2$ advances straight by transmitting through the dichroic mirror 26 and is irradiated to the second reference mirror 24.

Further, at each of the first and the second reference mirrors 23, 24, irradiated light is reflected in a direction inverse to an incident direction at reflecting faces thereof and advances inversely through the incident path as reference light. That is, whereas reference light from the first reference mirror 23 is deflected by 90 degrees again by the dichroic mirror 26 to reach the collimator 25, reference light from the second reference mirror 24 transmits through the dichroic mirror 26 to reach the collimator 25 and both fluxes of reference light are transmitted to the 2×2 coupler 22.

Although fluxes of detected light and reference light transmitted to the 2×2 coupler 22 in this way are combined with each other by the 2×2 coupler 22, fluxes of the combined two waves are provided with extremely short coherence lengths and therefore, the fluxes of combined two waves interfere with each other only when light delay amounts of the respectives are substantially equal to each other. Here, the interval $1_1$ between the first reference mirror 23 and the dichroic mirror 26 and the distance $1_2$ between the second reference mirror 24 and the dichroic mirror 26 are respectively set to specific values different from each other ($1_1 \neq 1_2$). Therefore, interference light produced between detected light centering on the wavelength $\lambda_1$ and reference light from the first reference mirror 23 and interference light produced between detected light centering on the wavelength $\lambda_2$ and reference light of the second reference mirror 24 respectively correspond to depth positions of the subject 71 different from each other.

Interference light provided by the 2×2 coupler is transmitted to the collimator 61 by way of the optical fiber.

Interference light transmitted to the collimator 61 is made to be parallel light thereby and irradiated to the diffraction grating 62. Interference light incident on the diffraction grating 62 is dispersed in wavelength and is reflected to the Fourier transformation lens 63. That is, for example, interference light having the central wavelength of $\lambda_1$ is incident on the Fourier transformation lens 63 by being dispersed from an optical axis of the Fourier transformation lens 63 to an upper side, further, interference light having the central wavelength of $\lambda_2$ is incident on the Fourier transformation lens 63 by being dispersed from the optical axis of the Fourier transformation lens 63 to a lower side, respectively.

Further, respective fluxes of interference light having the central wavelength $\lambda_1$ and the center wavelength $\lambda_2$ incident on the Fourier transformation lens 63 are subjected to Fourier transformation operation of the Fourier transformation lens 63 and irradiated to the optical detector 41.

For example, the line image sensor is used for the optical detector 41, as described above, interference light having the central wavelength $\lambda_1$ is dispersed to the upper side from the optical axis of the Fourier transformation lens 63. Further, interference light having the central wavelength $\lambda_2$ is dispersed from the optical axis of the Fourier transformation lens 63 to the lower side, respectively. Therefore, fluxes of interference light can be made to be incident on portions of the line image sensor different from each other for respective wavelength bands of the fluxes of interference light such that, for example, interference light having the central wavelength $\lambda_1$ is made to be incident on from the center to an upper side half of the line image sensor, at the same time, interference light having the central wavelength $\lambda_2$ is made to be incident on from a center to a lower side half of the line image sensor.

Light incident on the optical converter 41 is photoelectrically converted into optical intensity signals (interference fringes) for respective spectors and inputted to the signal processing portion 65. Here, an output signal from the optical converter 41 is outputted independently for each wavelength band in correspondence with the fact that the interference light is separated for each wavelength band as described above and irradiated to the optical detector 41.

Further, at the signal processing portion 65, by being subjected to a signal processing necessary for providing the one-dimensional tomographic image signal reflected with information in the depth direction of the subject 71 for each wavelength band, there are provided a one-dimensional tomographic image signal with regard to the central wavelength $\lambda_1$ (refer to a waveform diagram attached with notation I of FIG. 1) and a one-dimensional tomographic image signal with regard to the central wavelength $\lambda_2$ (refer to a waveform diagram attached with notation II of FIG. 1). Further, at the signal processing portion 65, two kinds of the one-dimensional tomographic image signals having different wavelength bands are added to each other to be outputted as a signal tomographic image signal (notation III of FIG. 3) and the signal is inputted to an image processing apparatus, not illustrated.

At the image processing apparatus, not illustrated, even the tomographic image signals simultaneously inputted with regard to the depth positions of the subject 71 different from each other are separated in accordance with a difference in the wavelength band to constitute an identifiable signal and therefore, the signals can respectively be displayed by images simultaneously.

Further, in the first embodiment, there may be constructed a constitution in which a circulator substitutes for the 2×2 coupler 22. Further, although the dichroic mirror 26 is used as the wavelength selecting element, naturally, the wavelength selecting element needs not to be limited thereto but the wavelength selecting element may be constructed by a constitution of using other optical element so far as the optical element is provided with a similar function.

Further, although according to the first embodiment, positions of arranging the first and the second reference mirrors 23, 24 are fixed, naturally, the first and the second reference mirrors 23, 24 are not limited to such a constitution but the first and the second reference mirrors 23, 24 may be made to be movable respectively in optical axis directions.

Figure 3:
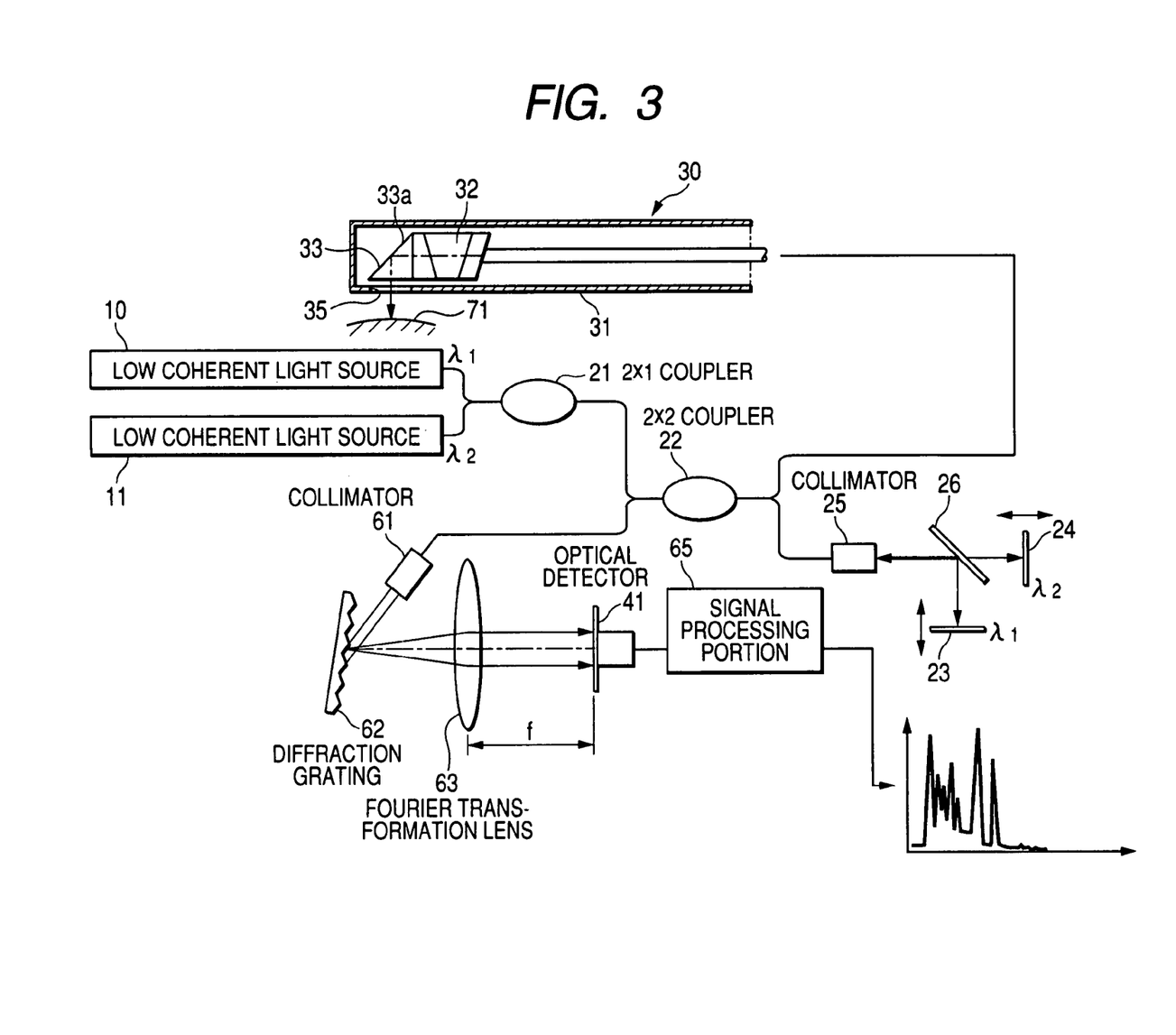
FIG. 3 is an outline view showing an optical tomographic apparatus according to an illustrative, non-limiting second embodiment of the invention.

FIG. 3 shows a constitution example of an optical tomographic apparatus according to an exemplary second embodiment when the first and the second reference mirrors 23, 24 are made to be movable respectively in optical axis directions and the second embodiment will be explained in reference to the drawing as follows. Further, constituent elements the same as those of the optical tomographic apparatus according to the above-described first embodiment are attached with the same notations and a detailed explanation thereof will be omitted and an explanation will be given centering on a point different therefrom.

In the optical tomographic apparatus according to the second embodiment, the first and the second reference mirrors 23, 24 are made to be movable respectively in optical axis directions. Here, it is sufficient that a moving mechanism (not illustrated) for moving the reference mirrors 23, 24 is constituted by a publicly known/well known constitution used in a background art apparatus.

In such a constitution, by pertinently moving the first and the second reference mirrors 23, 24 respectively, information of an interference wave having the central wavelength $\lambda_1$ and information of an interference wave having the central wavelength $\lambda_2$ are respectively provided with regard to a position in the depth direction of the subject 71 in accordance with moved positions thereof.

Further, in the second embodiment, particularly when the distances between the first and the second reference mirrors 23, 24 and the dichroic mirror 26 are set to be the same, with regard to the same position in the depth direction of the subject 71, information of the interference wave having the central wavelength $\lambda_1$ and information of the interference wave having the central wavelength $\lambda_2$ are respectively provided. That is, a spectroscopic characteristic can be provided with regard to a desired portion in the depth direction of the subject 71 and by analyzing the spectroscopic characteristic, various states of the subject 71 can be known. Further, in FIG. 3, as a waveform diagram of an output signal of the signal processing portion 65, there is schematically shown a waveform diagram when the distances between the first and the second reference mirrors 23, 24 and the dichroic mirror 26 are set to be the same.

Further, in both of the first and the second embodiments, the subject 71 is not limited to the human body but can be constituted by other various tissues in which fluxes of reflected light can be provided from respective positions at inner portions thereof.

Further, although in any of the above-described embodiments, the light source portion is constituted by the two low coherent light sources 10, 11 independent from each other, there may be constructed a constitution in which two or more of independent low coherent light sources having wavelength bands different from each other are used, a wavelength selecting element is made to correspond to a number of wavelength bands thereof and also reference mirrors are provided in accordance with a number of wavelength bands. Further, there may naturally be constructed a constitution of using a single light source capable of simultaneously outputting a plurality of fluxes of low coherent light having wavelength bands different from each other.

There are examples of optical tomographic apparatus using a plurality of light sources as in the invention disclosed in, for example, JP-A-2003-254898, JP-A-2003-307485 and the like, although the apparatus the same as the invention in that the plurality of light sources are used, the apparatus are quite different from the thought of the invention which proposes a method, means for achieving the object of providing low coherent light having a short coherent length in comparison with a case of using the single light source by providing combined light of the plurality of light sources and in which by fluxes of low coherent light having different wavelength bands, information of fluxes of interference light from portions of the subject having different depths are simultaneously provided, or information of a useful spectroscopic characteristic based on information of different wavelengths from the portion at the same depth of the subject is provided and do not suggest any of the technical thought of the invention.

While the invention has been described in detail and with reference to specific embodiments thereof, it will be apparent to one skilled in the art that various changes and modifications can be made therein without departing from the spirit and scope thereof.

The present application claims foreign priority based on Japanese Patent Application No. JP2004-352458 filed Dec. 6, 2004, the contents of which is incorporated herein by reference.

What is claimed is:

1. An optical tomographic apparatus comprising:

a light source that emits light having low coherence in at least two wavelength bands different from each other;

an interferometer that: divides a flux of the light emitted from the light source into two fluxes; irradiates a subject with one of the two fluxes; irradiates a reference face with the other of the two fluxes; combines a flux of light reflected from the reference face and a flux of light reflected from the subject so as to obtain interference light; and provides an optical intensity distribution of the interference light by an optical detector; and a signal processing unit that provides a tomographic image signal based on a signal of the optical intensity distribution, wherein the interferometer comprises: a wavelength selecting element that separates the flux irradiated to the reference face into a first flux of light in a first wavelength band and a second flux of light in a second wavelength band without producing a phase shift therebetween; a first reflection optical element having the reference face for the first flux; and a second reflection optical element having the reference face for the second flux, and the signal processing unit generates the tomographic image signal with respect to each of the at least two wavelength bands of the light emitted from the light source, and outputs a combined signal thereof.

2. The optical tomographic apparatus according to claim 1, wherein the at least two wavelength bands include the first and second wavelength bands.

3. The optical tomographic apparatus according to claim 1, wherein the optical detector comprises a line image sensor, the interferometer comprises a spectroscopic optical system for separating the interference light, and the line image sensor is irradiated with the interference light by way of the spectroscopic optical system so as to be able to detect the interference light separated for each of the at least two wavelength bands of the light source.

4. The optical tomographic apparatus according to claim 1, which comprises a moving mechanism for each of the reflection optical elements, wherein the moving mechanism moves the reflection optical element in a direction along an optical axis of the reflection optical element so that an optical path length of the light reflected from the reference face is able to be changed for each of the first and second wavelength bands.

5. The optical tomographic apparatus according to claim 1, wherein the light source comprises: a source emitting first light in the first wavelength band; and a source emitting second light in the second wavelength band, and the light emitted from the light source includes the first and second lights.

* * * * *